Figure 1:
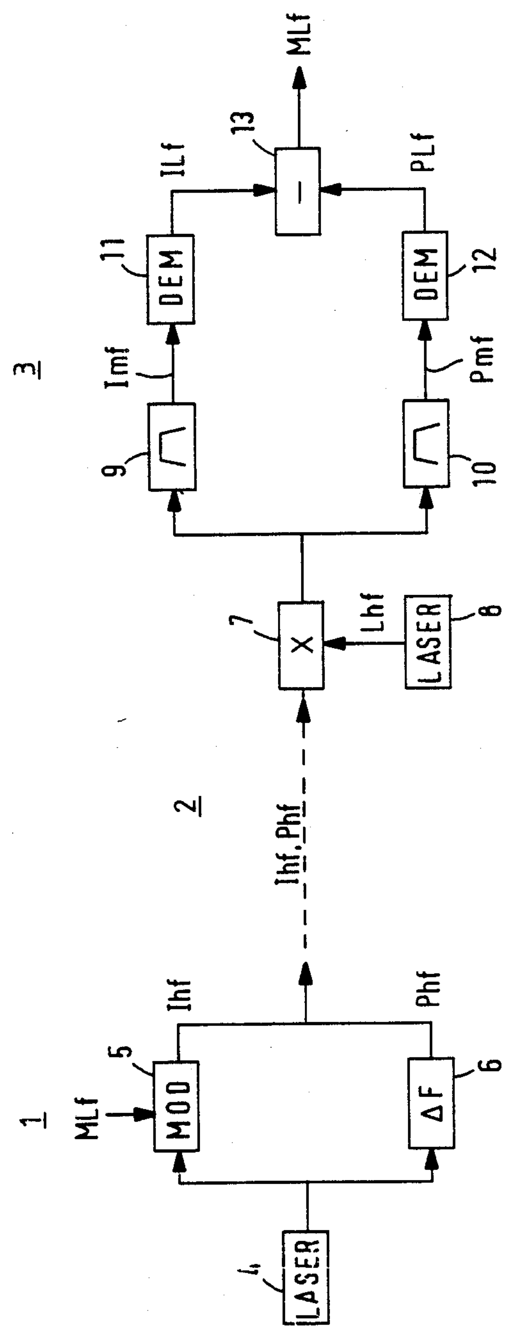

United States Patent [19]

Bekooij

[11] Patent Number: 4,918,747

[45] Date of Patent: Apr. 17, 1990

[54] METHOD AND DEVICE FOR COMPENSATING, IN A COHERENT OPTICAL COMMUNICATION SYSTEM WITH HETERODYNE DETECTION, AT THE RECEIVING SIDE, PHASE NOISE OF A TRANSMITTING LASER AND OF A LOCAL LASER

[75] Inventor: Johan P. Bekooij, Zoeterwoude-Rijndijk, Netherlands

[73] Assignee: Staat Der Nederlanden, The Hague, Netherlands

[21] Appl. No.: 289,624

[22] Filed: Dec. 23, 1988

[30] Foreign Application Priority Data

Jan. 12, 1988 [NL] Netherlands ........................ 8800067

[51] Int. Cl.[4] ........................................ H04B 9/00

[52] U.S. Cl. .................................... 455/617; 455/618

[58] Field of Search ............... 455/600, 606, 607, 608, 455/609, 610, 611, 612, 617, 618, 619, 616

[56] References Cited

U.S. PATENT DOCUMENTS 4,783,852 11/1988 Auracher ........................... 455/619

FOREIGN PATENT DOCUMENTS 0234744 9/1987 European Pat. Off. .

0251062 1/1988 European Pat. Off. ........... 455/619

54-114005 11/1979 Japan .

OTHER PUBLICATIONS

Hodgkinson, "Demodulation of Optical DPSK using in-plase and Quadrative Detection", Electronic Letters, 9-12-85, Vol. 21 #18.

*Primary Examiner*—Robert L. Griffin

*Assistant Examiner*—L. Van Beek

*Attorney, Agent, or Firm*—Frishauf, Holtz, Goodman & Woodward

[57] ABSTRACT

The invention relates to a method for compensating, in a coherent optical communication system with heterodyne detection, at the receiving side phase noise of the transmitting and of the local laser. Characteristic of the present method is that the phase-noise compensation takes place in the LF domain. The two MF heterodyne signals (Imf and Pmf) are first demodulated into LF signals (in which there is still noise), which are subsequently subtracted from one another, due to which the respective noise components cancel out each other. Preferably a local laser signal which is, qua frequency, between the two other HF signals is chosen. This offers the advantage that the two MF heterodyne signals can be modulated by one and the same demodulator; because for the compensation of phase noise the demodulated MF signals (Iif respectively Pif) which are, qua phase noise, in opposite phase with regard to each other are then added to one another.

The advantage of the method according to the invention is that the bandwidth for which the receiver has to be suitable is relatively small.

6 Claims, 2 Drawing Sheets

1 MLf 5 MOD Ihf 2 4 LASER Ihf.Phf ΔF Phf 6 3 9 Imf 11 DEM ILf 7 X 13 − MLf Lhf LASER 8 10 Pmf 12 DEM PLf

METHOD AND DEVICE FOR COMPENSATING, IN A COHERENT OPTICAL COMMUNICATION SYSTEM WITH HETERODYNE DETECTION, AT THE RECEIVING SIDE, PHASE NOISE OF A TRANSMITTING LASER AND OF A LOCAL LASER

A. BACKGROUND OF THE INVENTION

1. Field of the invention

The invention relates to a method for compensating phase noise, generated by lasers, in a coherent optical communication system, which comprises an optical transmitter with a transmitting laser for generating an HF information signal which is formed by a carrier wave modulated by information, as well as for generating an HF pilot signal which is formed by an unmodulated carrier wave, which two HF signals are transmitted via a transmission medium, an optical receiver for receiving said HF signals via said transmission medium, which receiver is provided with a heterodyne circuit comprising a local laser for generating a local HF signal, a mixer circuit for mixing this local HF signal with the HF signals received, and at least one MF filter circuit for letting pass only an MF information signal corresponding to the HF information signal and an MF pilot signal corresponding to the HF pilot signal. The abbreviations "HF ", "MF" and "LF" used above and likewise the corresponding abbreviations "hf", "mf" and "lf" used in the drawings, respectively signify "high frequency", "medium frequency" and "low frequency". These terms are common for describing heterodyne detection, although "intermediate frequency" is perhaps more widely used than "medium frequency". The HF frequency range accordingly means the frequency range a signal before heterodyne detection and the LF frequency range signifies the frequency range of a detected signal after heterodyne detection.

2. State of the art

The performances of coherent optical communication systems can be seriously affected by the phase noise of the lasers. In consequence of this the achievable signal/noise ratio (or "bit error rate") will generally be limited and the sensitivity of the receiver will degrade. The linewidth (spectral bandwidth) of DFB-lasers (DFB: Distributed Feedback) is of the order of 10 MHz and for MEC-DFB-lasers (MEC: Monolitical External Cavity) of the order of 1 MHz. Linewidths in the kHz-area can be realized by means of long external cavities; suchlike large lasers are, however, not suited for being used on a large scale in coherent communication networks.

The fact that in high-quality coherent systems DFB-lasers can only be used for transmission speeds of more than some Gbits/s is caused by the phase noise in such lasers. Moreover, the synchronous modulation will be seriously hindered by the practical implementation of PLLs with the required natural frequencies (some 100 MHz).

From the above it will be clear that techniques for suppressing phase noise in coherent optical communication systems are of great importance. These techniques can be subdivided into:

spectral purification [I], in which case reduction of phase noise is effected directly at the laser sources;

compensation [II], in which case the phase noise at the receiving side is suppressed, after heterodyne detection, by means of signal processing.

[I]Spectral purification can be achieved by optical feedback [a], electrical feedback [b] and optical filtering [c].

[a]Optical feedback is used in extended cavity structures;

[b]Electrical feedback stabilizes the laser using optical frequency discrimination (AFC) [ref. 1, 2]. Although a narrowing of the linewidth can be achieved, the phase noise reduction is restricted to frequencies within the bandwidth of the feedback circuit [ref. 3]. Consequently, the performances of such a coherent system will remain limited [ref. 4];

[c]Optical filtering cuts off the phase noise in the spectral sidebands of the optical carrier wave by means of a band-pass filter (e.g. a glass-fibre filter according to Fabry-Pérot).

[II]Compensation techniques make use of an unmodulated pilot-carrier wave (pilot signal) which is sent along with the signal modulated by information (information signal). The pilot signal can be derived from the transmitting laser preceding the modulation by the information to be transmitted. By means of a frequency shift with regard to the carrier wave of the information signal it will be possible to separate at the pilot signal from the information signal at the receiving side. Another possibility is orthogonal polarization of the information signal and of the pilot signal with respect to each other [7]. After heterodyne detection — by means of the local laser — phase-noise compensation will be effected by means of signal processing. For this purpose it is known to make use of non-linear heterodyne detection. In this case the two MF signals — coming from the HF information signal and from the HF pilot signal — are multiplicatively mixed in a mixer. After unwanted mixture products have been filtered away by a filter, the result will be a phase-noise compensated MF signal; the elimination of the phase noise is the result of the fact that the filter lets pass only the MF mixer signal in which the respective noise components — mathematically represented — cancel out each other. After this the 13 low phase-noise - MF signal will be demodulated into an LF signal [ref. 5, 6] in the known way. A drawback of the known compensation method is the relatively large bandwidth required because of the fact that the frequency distances between the HF information signal, the HF pilot signal and the signal of the local (heterodyne) laser have to be so great that the unwanted mixture products can be filtered out. This relatively large bandwidth has especially repercussions on the properties of the HF amplifier of the receiver.

B. SUMMARY OF THE INVENTION

The present invention provides a method for compensating phase noise — as described under A1 — which has the advantage that the required bandwidth can be considerably smaller than in the case of the known method. The essence of the invention is that the phase-noise compensation takes place in the LF domain instead of — according to the known method — in the MF domain.

The method according to the present invention is characterized in that each of said MF signals — the MF information signal and the MF pilot signal — is demodulated into a corresponding LF signal, and in that these LF signals — dependent on their phase relation to one another — are linearly subtracted from one another or added to one another. The LF information signal consists of the sum of the LF information by which the HF information signal was modulated at the transmitting side and the LF phase noise, whereas the LF pilot signal consists of only phase noise. If these LF signals are in phase, they will be subtracted from one another; if they are in opposite phase, they will be added to one another. So, in both cases the LF pilot signal — equal to the LF phase noise — will be subtracted from the LF information signal — equal to the information transmitted plus the LF phase noise — due to which "clean" information will remain. The amplitudes of the MF information signal and of the pilot signal have, however, to be adjusted in the correct ratio.

The present invention also provides an optical receiver for a coherent optical communication system in which this method is employed comprising an optical transmitter in which a transmitting laser capable of transmitting both an HF information signal modulated on an HF carrier wave as well as an HF pilot signal which is a separate unmodulated wave, both these waves being transmitted optically from the same installation. Such a system also comprises, in accordance with the invention, an optical receiver provided with a heterodyne circuit in which a local laser generates a local HF signal that is mixed in a mixer circuit in which both the received HF signals are converted into corresponding LF signals and MF filter circuits are provided for the MF information and pilot signals. More particularly, and in which the MF information signal and the MF pilot signal are fed to one or more demodulation circuits in which these MF signals are converted into corresponding LF signals which are subtracted from one another due to which a low phase-noise output signal will be formed.

As regards frequency the local HF signal will be between the HF information signal and the HF pilot signal. Owing to this it is achieved that due to the "mirror effect" the LF phase-noise component in the LF information signal will be in opposite phase with the LF phase-noise component of the LF pilot signal. Now the phase noise will be compensated by adding these respective LF phase-noise components to one another. This method has the advantage that in an optical receiver in which this preferred method is employed both the MF information signal and the MF pilot signal can be fed to one common demodulation circuit, in which the MF signals will be modulated and moreover simultaneously added to one another. In this way it is achieved that by means of rather few components a low phase-noise output signal can be taken off.

C. REFERENCES

[1] Ohtsu, M.; Kotajima, S. Linewidth reduction of a semiconductor laser by electrical feedback IEEE J. Quantum Electron (USA). vol. Qe-21, no. 12, pp. 1905–12, Dec. 1985, 20 REF.

[2] Yamamoto, Y.; Nilsson, 0.; Saito, S. Theory of a negative frequency feedback semiconductor laser IEEE J. Quantum Electron. (USA), vol. QE-21, no. 12, pp. 1919–28, Dec. 1985, 21 REF.

[3] Glance, B. Performance of AFC for phase noise reduction of optical sources Electron. Lett. (GB), vol. 21, no. 21, pp. 994–5, 10 Oct. 1985, 1 REF.

[4] Kikuchi, K.; Lee, T.P. Design theory of electrically frequency-controlled narrow-linewidth semiconductor lasers for coherent optical communication systems J. Lightwave Technol. (GB), vol. LT-5, no. 9, pp. 1273–6, Sep. 1987

[5] Dakin, J.P.; Wade, C.A.; Ellis, G.H. A novel 3-wave mixing heterodyne approach to coherent optical communications Proc. ECOC, 1986, pp. 33–7

[6] Bondurant, R.S.; Welford, D.; Alexander, S.B.; Chan, V.W.S. Frequency-noise cancellation in semiconductor lasers by nonlinear heterodyne detection Opt. Lett. (USA), vol. 11, no. 12, pp. 791–3, Dec. 1986, 5 REF.

[7] Calvani, R.; Caponi, F.; Cisternino, F. Coherent transmission insensitive to laser phase noise by polarization modulation and differential heterodyne detection Proc. ECOC, 1987, pp. 9–12.

D. EMBODIMENTS

1. Figures

Figure 1A:
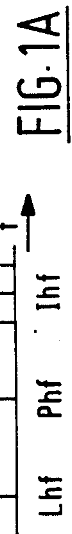

FIG. 1 shows a first embodiment of the invention, in which at the receiving side the MF information signal and the MF pilot signal are separately demodulated, after which the LF signals thus formed will be subtracted from one another. FIG. 1A shows the position of the various H in the HF spectrum.

Figure 2:
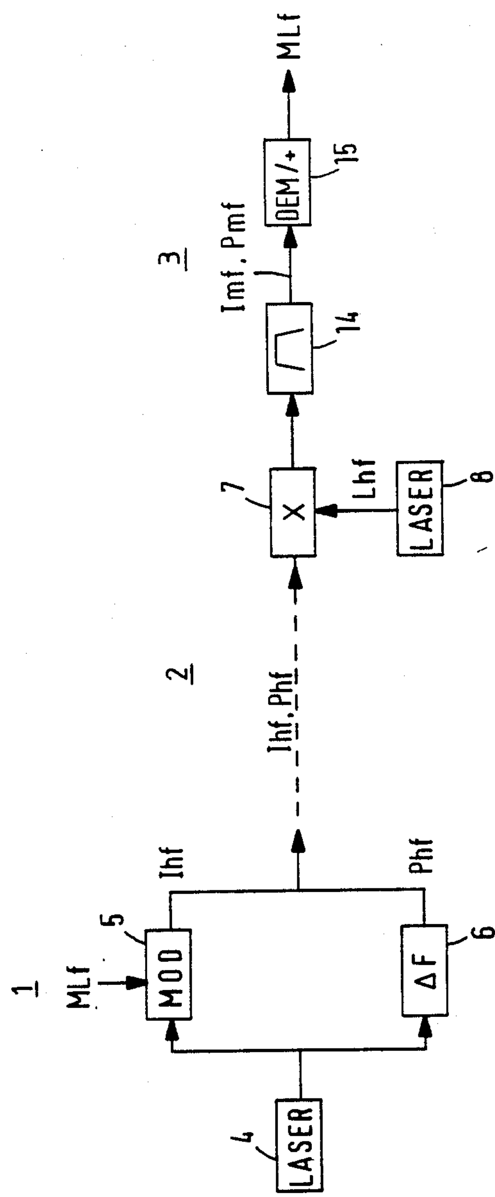

FIG. 2 preferred embodiment of the invention, in which at the receiving side the MF signals can be demodulated in one demodulator and the LF signals can be added to one another, due to the position of the local HF signal between the position of the HF information signal and the position of the HF pilot signal.

Figure 2A:
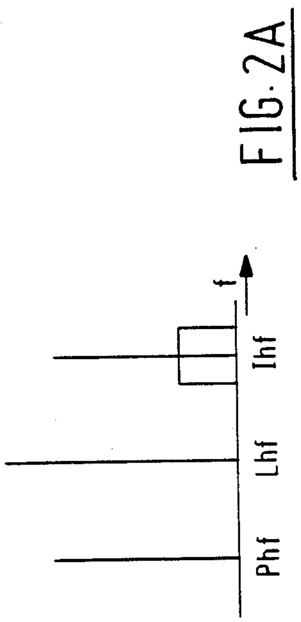

FIG. 2A shows the position of the various HF signals in the HF spectrum.

2. Description

FIG. 1, shows a coherent optical communication system formed by a transmitter 1, a transmission medium 2 and a receiver 3. The transmitter comprises a laser 4, which generates an optical HF signal, which is fed to a modulator 5, in which the HF signal is modulated by an LF modulation signal Mlf into an HF information signal Ihf. The HF signal generated by the laser 4 is also fed to a frequency shifter 6, which delivers an HF pilot signal Phf with a frequency which is a $\Delta f$ lower. The two HF signals — Ihf and Phf — are transmitted via the transmission medium 2 to the receiver 3, in which these HF signals will be mixed in a detector 7 with an HF signal of a local (heterodyne) laser 8 and converted into an electric mixer product. By means of a pair of band-bass filters 9 and 10 each of the desired MF signals — the MF information signal Imf and the MF pilot signal Pmf — will be fed to a demodulator 11 respectively 12. The demodulated signals — the LF information signal and the LF pilot signal — are fed to a difference circuit 13, which delivers the difference of the LF signals fed as an output signal. The working is as follows:

The HF signals of the transmitting laser 4 as well as of the local laser 8 comprise a phase-noise component. The phase noise of the transmitting laser 4 manifests itself both in the HF information signal Ihf and in the HF pilot signal Phf. The pilot signal (incl. phase noise) serves to compensate the phase noise at the receiving side — the phase noise not only coming from the transmitting laser, but also the phase noise introduced by the local laser — in the information signal. As described hereinabove the HF information signal and the HF pilot signal are divided at the receiving side into an MF information signal and an MF pilot signal by mixing and filtering. These MF signals — which both comprise MF phase noise — are subsequently demodulated, resulting in an LF information signal consisting of the original modulation signal Mlf plus the LF phase-noise component, as well as in an LF pilot signal which exclusively consists of the LF phase-noise component (since the HF pilot signal was not modulated at the transmitting side). By now subtracting in the difference circuit 13 the LF pilot signal (equal to the LF phase-noise component) from the LF information signal (equal to the original modulation signal Mlf plus the LF phase-noise component) the original modulation signal Mlf will remain.

FIG. 2 shows a simplification of the receiver 3, which has been achieved by generating a local laser signal Lhf the frequency of which is between the frequency of the HF information signal Ihf and the frequency of the HF pilot signal Phf. This is illustrated in FIG. 2_a_. The mixer product of the detector 7 will now be fed to only one band-pass filter 14, which lets pass the two desired MF signals — the MF information signal Imf and the MF pilot signal Pmf —. Because of the fact that the local laser signal Lhf is qua frequency between the HF information signal Ihf and the HF pilot signal Phf, the phase-noise component in each of the MF signals will be in opposite phase due to the "mirror effect". After demodulation of these MF signals the phase-noise component in the LF signals will also be in opposite phase; so phase-noise compensation can be achieved by adding the LF signals to one another instead of subtracting them from one another, as it is the case in the above-described embodiment. This adding of the LF signals will now simultaneously take place by presenting the two MF signals to one and the same demodulator 15. In this demodulator 15 the two MF signals will be demodulated into two LF signals — the LF information signal, consisting of the LF modulation signal plus the LF phase-noise component, respectively the LF pilot signal, consisting of the LF phase-noise component in opposite phase — and added to each other, thus resulting in the original LF modulation signal.

I claim:

1. Method for compensating phase noise, generated by lasers, in a coherent optical communication system, which comprises:

an optical transmitter with a transmitting laser for generating an HF information signal which is formed by a carrier wave modulated by information, as well as for generating an HF pilot signal which is formed by an unmodulated carrier wave, which two HF signals are transmitted via a transmission medium, an optical receiver for receiving said HF signals via said transmission medium, which receiver is provided with a heterodyne circuit comprising a local laser for generating a local HF signal, a mixer circuit for mixing this local HF signal with the HF signals received, and at least one MF filter circuit for letting pass only an MF information signal corresponding to the HF information signal and an MF pilot signal corresponding to the HF pilot signal, characterized in that the MF information signal (Imf) is demodulated into an LF information signal (Ilf) and the MF pilot signal (Pmf) into an LF pilot signal (Plf) in a manner whereby said LF information signal and said LF pilot signal have either a cophase of an antiphase relation to each other, and in that said LF signals — dependent on their cophase or antiphase relation to one another — are linearly substracted from one another or added to one another, thereby producing an LF signal of reduced phase noise.

2. Method according to claim 1, characterized in that the local HF signal (Lhf) is, of a frequency between the HF information signal (Ihf) carrier frequency and the HF pilot signal (Phf) frequency and in that said LF signals are added to one another.

3. Optical receiver for receiving HF signals in a coherent optical communication system which comprises an optical transmitter with a transmitting laser for generating an HF information signal which is formed by a carrier wave modulated by information, as well as for generating an HF pilot signal which is formed by an unmodulated carrier wave, which two HF signals are transmitted to said receiver via a transmission medium, which receiver is provided with a heterodyne circuit comprising a local laser for generating a local HF signal, a mixer circuit for mixing this local HF signal with the HF signals received and producing an MF information signal (Imf) and an MF pilot signal (Pmf), and further comprising:

MF filter circuit means (9, 10) connected to said mixer circuit for providing a first output at which a filtered MF information signal is made available and a second output at which a filtered MF pilot signal is made available;

a first demodulation circuit (11) having an input connected to said first output of said MF filter circuit means for converting the MF information signal into an LF information signal and (Ilf);

a second demodulation circuit (12) connected to said second output of said MF filter circuit means for converting said MF pilot signal into an LF pilot signal (Plf);

said first and second demodulation circuits being of a design whereby said LF information signal nd said LF pilot signal are either in phase with each other or of opposite phase to each other, and a combination circuit (13) for linearly subtracting said LF signals from one another or adding them to one another in accordance with whether they are cophased or antiphased to one another and thereby forming an LF output signal (Llf) of reduced phase noise.

4. Optical receiver according to claim 3, characterized in that the LF signals are in phase with one another and in that these signals are subtracted from one another in the combination circuit (13).

5. Optical receiver according to claim 3, characterized in that the LF siganls are in opposite phase with one another and in that these signals are added to one another in the combination circuit.

6. Optical receiver for receiving HF signals in a coherent optical communication system which comprises an optical transmitter with a transmitting laser for generating an HF information signal which is formed by a carrier wave modulated y information, as well as for generating an HF pilot signal which is formed by an unmodulated carrier wave, which two HF signals are transmitted to said receiver via a transmission medium, said receiver comprising:

a heterodyne circuit comprising a local laser (8) for generating a local HF signal (Lhf) of a frequency which is between the frequency of the carrier wave of said HF information signal (Ihf) and the frequency of said HF pilot signal (Phf);

a mixer circuit (7) for mixing said local HF signal with the said HF signals received and producing an MF information signal (Imf) and an MF pilot signal (Pmf);

bandpass filter means (14) for making available, at an output thereof, a filtered MF signal in which said MF information signal and said MF pilot signal are both present;

a demodulator (15) having an input connected to the output of said bandpass filter means (14) for converting said MF signals present in said filtered MF signal into corresponding LF signals and for simultaneously adding said LF signals to one another to form an output LF signal (Mlf) of reduced phase noise.

* * * * *

UNITED STATES PATENT AND TRADEMARK OFFICE

CERTIFICATE OF CORRECTION

PATENT NO. : 4,918,747

DATED : April 17, 1990

INVENTOR(S) : BEKOOIJ, Johan P.

It is certified that error appears in the above-identified patent and that said Letters Patent is hereby corrected as shown below:

Title page, under "OTHER PUBLICATIONS", insert the following:

Linewidth Reduction of a Semiconductor Laser by Electrical Feedback", IEEE Jurnal of Quantum Electronics, Vol. QE-21, No.12, pgs. 1905-12, December 1985.

"Theory of a Negative Frequency Feedback Semiconductor Laser", IEEE J. Quantum Electron, (USA), Vol. QE-21, No.12, pgs. 1919-28, December 1985.

"Performance of AFC for phase noise reduction of optical sources (IN Electron. Lett. (GB); Electron, Lett. Vol. 21, No.21, pgs. 994-5, October 10, 1985.

"Design theory of electrically frequency-controlled narrow-linewidth semiconductor lasers for coherent optical communication systems", Vol.LT-5, No.9, September 1987.

"A novel 3-wave mixing heterodyne approach to coherent optical communications", Vol. 3, pgs. 35-37; 1986.

"Frequency-noise cancellation in semiconductor lasers by nonlinear heterodyne detection, Vol. 11,December 1988; pgs. 791-793.

Coherent transmission insensitive to Laser phase noise... pgs.9-12; Vol. 3, 1987.

JAPANESE ABSTRACT from Japanese Publication 54-114005. Optical Communication System.

CERTIFICATE OF CORRECTION

PATENT NO. : 4,918,747

DATED : April 17, 1990

INVENTOR(S) : BEKOOIJ, Johan P.

It is certified that error appears in the above-identified patent and that said Letters Patent is hereby corrected as shown below:

Column 3, line 37, following "will", insert --preferably--.

Column 4, line 24, following "Fig.2", insert --shows a--.

Column 4, line 61, delete "the phase noise--.

Column 4, line 61, following "not only", insert --the phase noise--.

Column 6, line 38 (claim 3), change "nd" to --and--.

Signed and Sealed this

Eighth Day of September, 1992

*Attest:*

DOUGLAS B. COMER

*Attesting Officer*

*Acting Commissioner of Patents and Trademarks*